United States Patent
Choudary et al.

(10) Patent No.: US 6,794,521 B2
(45) Date of Patent: Sep. 21, 2004

(54) PROCESS FOR THE PREPARATION OF 2-NITROTHIOPHENE SELECTIVELY FROM THIOPHENE USING METAL EXCHANGED CLAY CATALYSTS

(75) Inventors: Boyapati Manoranjan Choudary, Andhra Pradesh (IN); Mannepalli Lakshmi Kantam, Andhra Pradesh (IN); Kompella Vishweshwar Ramprasad, Andhra Pradesh (IN); Kalluri Venkata Sri Ranganath, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 50 days.

(21) Appl. No.: 10/103,632

(22) Filed: Mar. 20, 2002

(65) Prior Publication Data

US 2003/0181734 A1 Sep. 25, 2003

(51) Int. Cl.$^7$ ............................................... C07D 31/38
(52) U.S. Cl. ...................................................... 549/68
(58) Field of Search ........................................... 549/68

(56) References Cited

U.S. PATENT DOCUMENTS 5,210,339 A   5/1993   Thomas et al. ............. 568/929
6,204,424 B1 * 3/2001   Yadav et al. ................ 585/502
6,376,726 B1 * 4/2002   Choudary et al. .......... 568/927

FOREIGN PATENT DOCUMENTS

WO    WO 94/19310    9/1994

OTHER PUBLICATIONS

Hartough et al, "Acylation studies in the thiophene and furan series . . . ", CA41:22391, 1947.*
Cornelis et al, "Regioselective liquid–phase toluene nitration with modified clays as catalysts", CA111:6976, 1989.*
Babsinian et al., *Org. Syn.*, 1943, 2:466–468.
Blatt et al., *J. Org. Chem.*, 1957, 22:1693—1695.
Levitt et al., *Anal. Chem.*, 1953, 25:196–197.
Levitt et al., *J. Am. Chem. Soc.*, 1954, 1951–1953.
Ostman et al., *Acta Chem. Scand.*, 1968, 22(5):1687–1689.
Smith et al., *J. Org. Chem.*, 1998, 63(23):8448–8454.
Wilhelm Steinkopf et al., *Annalen der Chemie*, 1933, 501:174–191.
Wilhelm Steinkopf, *Annalen der Chemie*, 1940, 545:38–45.

* cited by examiner

*Primary Examiner*—Deborah C. Lambkin
(74) *Attorney, Agent, or Firm*—Morgan & Finnegan, LLP

(57) ABSTRACT

The present invention provides an ecofriendly process for the preparation 2-nitrothiophenes selectively from thiophene, using metal exchanged clay catalysts and nitric acid, dispensing with the use of acetic anhydride.

13 Claims, No Drawings

PROCESS FOR THE PREPARATION OF 2-NITROTHIOPHENE SELECTIVELY FROM THIOPHENE USING METAL EXCHANGED CLAY CATALYSTS

FIELD OF THE INVENTION

The present invention relates to an ecofriendly process for the preparation 2-nitrothiophenes selectively from thiophene, using metal exchanged clay catalysts and nitric acid, dispensing with the use of acetic anhydride.

BACKGROUND OF THE INVENTION

Nitroheterocyclic compounds are important intermediates for drugs, pharmaceuticals and dyes. The chemistry of nitro-derivatives of many heterocyclic systems has long been established, but their commercial exploitation has developed only over the last 40 years. Synthetic nitrothiozoles like 2-acetylamino-5-nitrothiazole have antitrichomonal activity. In the 1940s, they were used for the treatment of war wounds. In 1947, the same drugs were found to be effective in the prevention of coccidiosis in chickens and enteritis in swine. These and other veterinary applications led to large volume usage in animal feed supplements. Thiophenes are used as chemotherapeutic agents although nifurzide obtained by condensation of 5-nitrothiophene-2-carboxylic acid hydrazide with 3-(2-nitro-5-furyl) acrolein contains both a nitrofuran and a nitrothiophene residue. Thiophene and its derivatives found applications in the pharmaceutical area over a wide range of drug types such as nonsteroidal, antiinflammatory, Rheumatoid and Osteoarthritis drugs, hypertension and heart drugs, antibiotics, antiglaucoma drug, veterinary products, agrochemical products and dyestuffs.

In the conventional nitration process, heterocyclic compounds such as furan, thiophene and pyrrole are nitrated by nitric acid and acetic anhydride.

Reference is made to Babasinian et al, Org. Syn. Coll., Vol.2, 466, 1943, wherein the nitration of thiophene is carried by reacting thiophene (0.63 mol) with fuming nitric acid (0.76 mol) in acetic anhydride-acetic acid solution at +10° C. to yield 85% of nitrothiophenes. Recrystallisation from hexane-isopropyl ether gave a nitrated product with the composition containing 85% of 2-nitrothiophene and 15% of 3-nitrothiophene. It is difficult to achieve the selectivity towards 2-nitrothiophene in the nitration of thiophene. The strongly electrophilic nitronium ion leads to significant yields of 3-isomer (12–15%). A preferred procedure is the slow addition of thiophene to an anhydrous mixture of nitric acid, acetic acid and acetic anhydride. The drawbacks are the use of expensive acetic anhydride, which is uneconomical and also exothermic and explosive nature of the reaction of acetic anhydride and nitric acid. Another draw back is the requirement for tedious separation of 2-nitrothiophene from 3-nitrothiophene in a low selective and high yield reaction.

Reference is made to Steinkopf, Ann., 545, 38, 1940 wherein the presence of 3-nitro-thiophene in the mononitration product from thiophene has been established. However, there has been no description of a procedure for obtaining the pure 2-nitrothiophene from the crude nitration product and for establishing the homogeneity of the 2-nitrothiophene.

Reference is made to Ostman et al, *Acta. Chem. Scand.,* 22, 1687, 1968 wherein to separate the mixture of 2-nitrothiophene and 3-nitrothiophene in its components, the isomers have instead been obtained through the selective chlorosulfonation of the 3-nitrothiophene which is possible due to the slow reactivity of 2-nitrothiophene over 3-nitrothiophene. The isomeric mixture of nitrothiophene obtained from nitration of thiophene was chlorosulfonated with chlorosulfonic acid at 40° C. and the course of the reaction was followed by NMR. The successful protocol for high isomeric purity 2-nitrothiophene (99%) from the 2- and 3-nitrothiphene mixture is as follows. Nitrothiophene (85:15) was dissolved in ethanol free from chloroform and transferred to a four-necked flask carrying a stirrer, refluxing condenser, dropping funnel and a thermometer. While keeping the flask at 40° C., chlorosulfonic acid was added over a period of 5 min. A sample of reaction mixture was withdrawn and used in order to follow the reaction by GC or NMR. When 3-nitrothiophene was consumed, the reaction mixture was poured into ice water. The chloroform layer was separated and the water phase was extracted with chloroform. The combined chloroform solutions were washed with water and then shaken with aluminium oxide. The solution was finally dried over sodium sulfate and the solvent was removed with a rotary evaporator. The residue was then recrystallised from hexane-isopropyl ether to get 99% pure 2-nitrothiophene. The drawback is the requirement of tedious separation of 2-nitrothiophene from 3-nitrothiophene.

Reference is made to Steinkopf et al, *Ann,* 501, 174, 1933 wherein 3-Nitrothiophene has higher melting point and is less soluble than the 2-nitro derivative and it can be purified easily by crystallization from ethanol.

Reference is made to Blatt et al, *J.Org.Chem.,* 22, 1693, 1957, wherein nitration of thiophene with nitric acid in the absence of acetic anhydride gave a mixture of products, viz., 2-nitrothiophene, 2,5-dinitrothiophene and 2,4-dinitrothiophene. The drawback is poor product selectivity making the separation process difficult.

Attempts to circumvent acetyl nitrate processes are reported to be both difficult and dangerous.

Reference is made to Levitt et al, *Anal. Chem.,* 25,196, 1953 wherein the action of nitric acid on thiophene results in the oxidative decomposition of the thiophene molecule, with apparently a quantitative conversion of the sulfur to sulfuric acid. The drawback is oxidative decomposition of the thiophene.

Reference is made to Levitt et al, *J.Am.Chem.Soc.,* 76, 1951, 1954 wherein they studied the nature of intermediate products and by-products of this interesting reaction. The products formed by the action of 8N nitric acid on thiophene in cyclohexane are 2-nitrothiophene, 2,5-dinitrothiophene, maleic acid, oxalic acid and sulfuric acid. The drawback is poor product selectivity to encumber difficult separation.

Reference is made to Smith et al, *J.Org.Chem,* 63, 8448, 1998 wherein thiophene is nitrated in excellent yields with regioselectivity under mild conditions using beta zeolite as a catalyst and a stoichiometric quantity of nitric acid and acetic anhydride. Thiophene gives a crude product that appeared to contain about 56% of the 3-nitro isomer and 44% of the 2-nitro isomer in an overall yield of about 80%. The drawbacks are the use of expensive acetic anhydride which is uneconomical and also exothermic and explosive nature of the reaction of acetic anhydride and nitric acid. Another draw back is the tedious separation of the 2-nitrothiophene from 3-nitrothiophene in a low selective and high yield reaction.

OBJECTS OF THE INVENTION

Accordingly, it is an object of the invention to provide a novel and ecofriendly process for the manufacture of 2-nitrothiophene dispensing with the use of acetic anhydride.

It is another object of the invention to provide a process for the manufacture of 2-nitrothiophene with >50% selectivity and good yield.

It is a further object of the invention to provide a process for the manufacture of 2-nitrothiophene which is carried out in a single step and is simple.

It is another object of the invention to provide a catalytic process for the manufacture of 2-nitrothiophene wherein the catalyst can be reused with consistent activity.

It is a further object of the invention to provide a process for the manufacture of 2-nitrothiophene which is clean, inexpensive and environmentally safe.

SUMMARY OF THE INVENTION

The above and other objects of the invention are achieved by preparing 2-nitrothiophene from thiophene with >50% selectivity, using solid acid catalysts.

Accordingly the present invention provides a process for the preparation of 2-nitrothiophene comprising nitrating thiophene using nitric acid in the presence of a solid acid catalyst selected from a montmorillonite clay catalyst and metal ion exchanged K10 montmorillonite clay catalyst, recovering nitrothiophene by concentration of the reaction mixture after separation of the catalyst.

In one embodiment of the invention, the nitration is carried out in the absence of acetic anhydride.

In another embodiment of the invention, the catalyst used is a solid acid catalyst comprising a metal ion exchanged clay.

In another embodiment of the invention, the metal ion is selected from the group consisting of $Fe^{3+}$, $Al^{3+}$, $La^{3+}$, $Cu^{2+}$ and $Zn^{2+}$.

In another embodiment of the invention, the molar ratio of nitric acid to thiophene is in the range between 1 to 2.

In another embodiment of the invention, the reaction time of nitration is in the range of 5–6 h.

In another embodiment of the invention, nitration is effected at a temperature in the range of 70–80° C.

In another embodiment of the invention, the selectivity to 2-nitrothiophene is 100%.

DETAILED DESCRIPTION OF THE INVENTION

Scientific Explanation

The novelty of the present invention with respect to prior art is to produce 2-nitrothiophene with >50% selectivity in the nitration of thiophene using solid acid catalysts selected from the group consisting of a montmorillonite clay catalyst and metal ion exchanged K10 montmorillonite clay catalysts using nitric acid as nitrating agent in place of hazardous nitric acid and acetic anhydride mixture. The >50% selectivity is possible by the use of metal exchanged montmorillonites of compatible pore dimensions designed and modified to direct the electrophile, nitronium ion to substitute at the 2-position due to pronounced ortho effect. Apart from generating nitronium ion, the solid acid catalyst also adsorbs the water formed during the reaction.

Clays exhibit both Bronsted and Lewis acidity. Montmorillonite after washing with mineral acids has surface acidities in between that of concentrated nitric and sulfuric acids. Cation exchange of the interstitial cations with transition metal ions, such as $Fe^{3+}$, $Zn^{2+}$ in montmorillonite clay also boosts the acidity. Both Bronsted and Lewis acidities play a vital role in the catalytic activity. Such acidities of the clay are expected to generate nitronium ion to trigger nitration reactions.

Acid treated montmorillonite commercially known as K10-montmorillonite, which has predominant Bronsted acid sites on broken edges is also a suitable catalyst for nitration reaction. The hydrated cations, the aqua complexes in montmorillonite, are more acidic than their corresponding homogeneous analogues. The enhanced density of Bronsted acidity is ascribed to the polarising influence of the cation in the water molecule in spatially restricted interlayers. The interlayer acidity increases with increasing ratio of charge to ionic radius of the cation. Further, exchanged metal also introduces Lewis acidity to the clay. The content of the metal and type of metal play a vital role in displaying Lewis acidity. After 5 h, $Fe^{3+}$-montmorillonite afforded 70% nitrothiophene with >50% selectivity to 2-nitrothiophene which is an unprecedented selectivity. When the reaction is continued for a further period of 1 h, i.e., for a total of 6 h, though the yield increases to 91%, selectivity to 2-nitrothiophene drops to 60%.

The following examples are given by way of illustration of the present invention and therefore should not be construed to limit the scope of the invention.

EXAMPLE 1

Preparation of the Catalyst a) The K10-montmorillonite purchased from Fluka chemicals was used as such.

b) Preparation of $Fe^{3+}$-montmorillonite: To a 1 lit. stirred aqueous solution of $FeCl_3$ (1.0 M), 80 g of K10 montmorillonite was added and the reaction slurry was stirred at ambient temperature for 16 h in order to saturate the exchange capacity of K10-montmorillonite. The clay suspension was centrifuged and the supernatant solution was discharged. The clay catalyst was filtered, washed with distilled water and washing cycles were repeated until the disappearance of chloride ions from the discarded water. The catalyst $Fe^{3+}$-montmorillonite thus obtained was dried overnight in an oven at 120° C. and finely ground in a mortar. Metal-ion exchanged clays such as $Fe^{3+}$, $Al^{3+}$, $La^+$, $Cu^{2+}$ and $Zn^{2+}$ catalysts were prepared in a similar procedure by dissolving the corresponding metal salts using conventional processes.

EXAMPLE 2

A mixture of thiophene (20 mmol, 1.68 g) and $Fe^{3+}$-montmorillonite (0.5 g) in dichloroethane (10 ml) was stirred under reflux in a three-necked round-bottomed flask (50 ml). Nitric acid (40 mmol, 1.8 ml) was added drop-wise to the mixture under continuous stirring. After 5 h, (followed by GC), the reaction mixture was filtered and concentrated to get the product. Yield 1.8 g.

EXAMPLE 3

A mixture of thiophene (20 mmol, 1.68 g) and $Fe^{3+}$-montmorillonite (0.5 g) in dichloroethane (10 ml) was stirred under reflux in a three-necked round-bottomed flask (50 ml). Nitric acid (40 mmol, 1.8 ml) was added drop-wise to the mixture under continuous stirring. After 6 h (followed by GC), the reaction mixture was filtered and concentrated to get the product. Yield 1.55 g

EXAMPLE 4

A mixture of thiophene (20 mmol, 1.68 g) and K10-montmorillonite (0.5 g) in dichloroethane (10 ml) was stirred under reflux in a three-necked round-bottomed flask (50 ml). Nitric acid (40 mmol, 1.8 ml) was added drop-wise to the mixture under continuous stirring. After 6 h (followed by GC), the reaction mixture was filtered and concentrated to get the product. Yield 2.066 g.

TABLE 1

NITRATION OF THIOPHENE BY METAL EXCHANGED CLAY CATALYSTS

| Example | Name | Catalyst | Temp. (° C.) | Time (h) | Conversion[a] (%) | Selectivity (%) |
|---|---|---|---|---|---|---|
| 2 | Thiophene | $Fe^{3+}$-mont. | 80 | 5 | 70[b] | 100 |
| 3 | Thiophene | $Fe^{3+}$-mont. | 80 | 6 | 91 | 60 |
| 4 | Thiophene | K10 mont. | 80 | 6 | 80 | 77 |

[a]determined by GC
[b]isolated yield

ADVANTAGES OF THE INVENTION

1. A novel and ecofriendly process for the manufacture of an important compound nitrothiophene.
2. The present process eliminates the use of acetic anhydride.
3. The yields are good with 100% selectivity to 2-nitrothiophene.
4. Nitration process is carried out in a single step and is simple. Elimination of additional steps such as isomer separation and filtration.
5. Reusability of the catalyst with consistent activity.
6. The present process is clean, inexpensive and environmentally safe since there is no effluent problem.

We claim:

1. A process for the selective preparation of 2-nitrothiophene, wherein the selectivity is >50%, comprising nitrating thiophene using nitric acid in the presence of a solid acid catalyst and an organic solvent, said solid acid catalyst being selected from the group consisting of a montmorillonite clay catalyst and a metal ion exchanged K10 montmorillonite clay catalyst, recovering 2-nitrothiophene by concentration of the reaction mixture separation of the catalyst, said process being carried out in the absence of an anhydride.

2. A process according to claim 1 wherein the solid acid catalyst is a metal ion exchanged K10 montmorillonite clay.

3. A process according to claim 2 wherein the metal ion is selected from the group consisting of $Fe^{3+}$, $Al^{3+}$, $La^{3+}$, $Cu^{2+}$ and $Zn^{2+}$.

4. A process according to claim 1 wherein the molar ratio of nitric acid to thiophene is in the range between 1 to 2.

5. A process according to claim 1 wherein the time of nitration is in the range of 5–6 h.

6. A process according to claim 1 wherein nitration temperature is in the range of 70–80° C.

7. A process according to claim 1 wherein the organic solvent is dichloroethane.

8. A process according to claim 1 wherein the selectivity to 2-nitrothiophene is 100%.

9. A process according to claim 1 wherein recovery of nitrothiophene is carried out by concentration of the reaction mixture after separation of the catalyst by filtration.

10. A process according to claim 1 wherein the metal ion exchanged montmorillonite clay is selected from the group consisting of $Fe^{3+}$, $Co^{2+}$, $Cu^{2+}$, $Zn^{2+}$, $Al^{3+}$, $Ce^{3+}$ and $La^{3+}$-montmorillonite clays.

11. A process according to claim 1 wherein the catalyst is recycled after separation.

12. A process for the preparation of 2-nitrothiophene with >50% selectivity from thiophene, which comprises nitrating thiophene in an organic solvent using nitric acid and in the absence of acetic anhydride, the molar ratio of nitric acid to thiophene being 1:2, in the presence of a solid acid catalyst consisting of $Fe^{3+}$ ion exchanged montmorillonite clay at a temperature of 80° C. and recovering 2-nitrothiophene by concentrating the reaction mixture after separation of the catalyst.

13. A process according to claim 12 wherein the organic solvent is dichloroethane.

* * * * *